US011382802B2

(12) United States Patent
Jang (10) Patent No.: US 11,382,802 B2
(45) Date of Patent: Jul. 12, 2022

(54) NON-SLIP COTTON SANITARY PAD

(71) Applicant: Youngmin Jang, Toronto (CA)

(72) Inventor: Youngmin Jang, Toronto (CA)

( * ) Notice: Subject to any disclaimer, the term of this patent is extended or adjusted under 35 U.S.C. 154(b) by 569 days.

(21) Appl. No.: 16/294,143

(22) Filed: Mar. 6, 2019

(65) Prior Publication Data

US 2020/0138647 A1 May 7, 2020

(51) Int. Cl.
*A61F 13/15* (2006.01)
*A61F 13/56* (2006.01)
*A61F 13/47* (2006.01)
*A61F 13/53* (2006.01)
*A61F 13/78* (2006.01)
*A61F 13/511* (2006.01)
*A61F 13/514* (2006.01)
*A61F 13/472* (2006.01)

(52) U.S. Cl.
CPC ........ *A61F 13/5616* (2013.01); *A61F 13/472* (2013.01); *A61F 13/4704* (2013.01); *A61F 13/511* (2013.01); *A61F 13/51405* (2013.01); *A61F 13/53* (2013.01); *A61F 13/78* (2013.01); *A61F 2013/530029* (2013.01); *A61F 2013/53035* (2013.01)

(58) Field of Classification Search
CPC .............. A61F 13/5616; A61F 13/4704; A61F 13/472; A61F 13/511; A61F 13/51405; A61F 13/78; A61F 2013/530029; A61F 2013/53035
See application file for complete search history.

(56) References Cited

U.S. PATENT DOCUMENTS

| 3,888,255 A | * | 6/1975 | Shah ................... A61F 13/5611 604/369 |
| 4,573,987 A | | 3/1986 | Lamb, Jr. |
| 4,834,739 A | * | 5/1989 | Linker, III ............ A61F 13/476 604/385.04 |
| 5,011,480 A | * | 4/1991 | Gossens .............. A61F 13/4752 604/385.23 |
| 2009/0306616 A1 | * | 12/2009 | Wennerback ..... A61F 13/15203 604/367 |
| 2019/0000693 A1 | | 1/2019 | Shima et al. |

FOREIGN PATENT DOCUMENTS

| CN | 105581870 A | 5/2016 |
| EP | 2799050 A1 | 11/2014 |
| KR | 1995-0003985 Y1 | 5/1995 |
| KR | 2020100006783 U | 7/2010 |
| WO | 2009/101542 A2 | 8/2009 |

\* cited by examiner

*Primary Examiner* — Jacqueline F Stephens
(74) *Attorney, Agent, or Firm* — The Dobrusin Law Firm, PC (57) ABSTRACT

Disclosed is a non-slip cotton sanitary pad, including a pad body, configured such that a cotton lining, an absorption pad and a waterproof cover are sequentially stacked, and a pair of wings protruding from both sides of the pad body, wherein the pair of wings protruding from both sides of the pad body includes a fastener so that the wings are fastened together in a folded state on the same surface, the cotton sanitary pad is disposed such that the waterproof cover contacts underwear, and the waterproof cover includes a non-slip member on the surface contacting the underwear.

20 Claims, 8 Drawing Sheets

NON-SLIP COTTON SANITARY PAD

BACKGROUND OF THE INVENTION

1. Technical Field

The present invention relates to a non-slip cotton sanitary pad, including a pad body, configured such that a cotton lining, an absorption pad and a waterproof cover are sequentially stacked, and a pair of wings protruding from both sides of the pad body, in which the pair of wings protruding from both sides of the pad body includes a fastener so that the wings are fastened together in a folded state on the same surface, the cotton sanitary pad is disposed such that the waterproof cover contacts underwear, and the waterproof cover includes a non-slip member on the surface contacting the underwear.

2. Description of the Related Art

Recently, due to the controversy over the harmful effects of a polymer absorbent, which is a chemical substance used in disposable sanitary napkins, on human bodies, cotton sanitary napkins that do not contain chemical products such as polymer absorbents or waterproof sheets and that may decrease the use of disposable products are receiving a great deal of attention.

Conventional disposable sanitary napkins are focused on the convenience of preventing menstrual blood from leaking while being capable of absorbing an excess of menstrual blood, and thus inevitably contain chemical substances. A sanitary napkin is configured to include an absorbent component that absorbs menstrual blood, a waterproof sheet that surrounds the absorbent component, and a lining that comes into direct contact with the human body. The lining that comes into direct contact with the human body is configured to be soft and feel good to the touch so as not to harm the human skin, but is problematic in that harmful volatile organic substances are released owing to the use of chemical fibers advantageous from the aspects of manufacturing costs and processing costs.

Furthermore, the lining of the disposable sanitary napkin is limited in improving the quality thereof from the viewpoint of disposable use, and is thus problematic in that a weakly durable material or a chemical fiber material is used, undesirably causing a rash on the skin in direct contact therewith. Upon general use, since sanitary napkins should be worn for about 4 days to 10 days, skin rashes or scratches due to continuous contact with the skin may occur, even in consideration of the replacement cycle.

Moreover, in order to fix the sanitary napkin to the underwear, it is common to use an adhesive made of an organic chemical substance having high fixing capability and high detachment capability considering the price from the viewpoint of disposable use, and the harmfulness of conventional disposable sanitary napkins has reached a serious level.

With regard thereto, many users who have been using disposable sanitary napkins for many years suffer from various symptoms such as menstrual irregularities, atopy, and skin sensitization.

Through various articles and experiments and opinions of actual users, the issue of harmfulness of disposable sanitary napkins has been continuously raised, but users have begun to pay attention to cotton sanitary napkins as a new workaround, rather than expecting to improve the quality of disposable sanitary napkins.

Among users who complain of symptoms such as menstrual irregularity or skin sensitization due to the use of disposable sanitary napkins, the observation that these symptoms are significantly reduced upon using cotton sanitary napkins has spread, and thus the popularity of cotton sanitary napkins is growing even more rapidly.

The cotton sanitary napkin is not discarded after a single use, but may be reused after being washed, and is configured such that the lining of the disposable sanitary napkin is replaced with cotton, and particularly, the absorbent component for absorbing menstrual blood is replaced with a natural component harmless to the human body, such as a cotton swab, instead of an organic substance such as a polymer absorbent, and a waterproof cover of a cloth material is further provided thereto. Therefore, the cotton sanitary napkin has an advantage that it may reduce the generation of volatile organic substances derived from the lining of the sanitary napkin and the absorbent component, and may also include the cotton lining, thus preventing damage to the skin. Furthermore, when the cotton lining is used, the user may feel the same tactile sensation as cotton underwear, thus exhibiting superior fineness of use compared to disposable sanitary napkins including a sheet material.

Meanwhile, the disposable sanitary napkin is easily attached to the underwear by means of an adhesive member provided to the outer surface of the waterproof sheet, that is, to the portion contacting the underwear, and in particular, even when the user who wears the disposable sanitary napkin moves or acts, menstrual blood may be stably absorbed and may be effectively prevented from leaking. However, the cotton sanitary napkin is repeatedly used after being washed based on the properties of the material thereof and thus has a limitation in that it is impossible to add an adhesive member for a disposable product, such as an adhesive or double-sided tape. Hence, the cotton sanitary napkin is provided with a pair of wings having snap buttons on both sides thereof, and the wings are folded so as to be positioned on the surface of the underwear opposite the surface contacting the sanitary napkin and are then fixed with the snap buttons.

However, when the sanitary napkin is fixed by the wings having the snap buttons, the movement of the sanitary napkin in the direction in which the wings protrude may be somewhat prevented, but there is no means for preventing movement in the direction perpendicular to the direction in which the wings protrude, that is, in the front and back directions of the human body, in the state of wearing the sanitary napkin.

In particular, contemporary women who repeatedly stand and sit frequently suffer from menstrual blood leakage to the rear, especially the hips, and it is essential to prevent the longitudinal movement of the cotton sanitary napkin because menstrual blood may leak more frequently upon forward movement of the sanitary napkin.

Nevertheless, the development of cotton sanitary napkins to solve this problem has not reached a satisfactory level, and it is necessary to overcome the problem of frequent menstrual blood leakage due to the longitudinal movement of the cotton sanitary pad in daily life such as walking or upon rolling about on the bed for the cotton sanitary napkin users.

With the goal of solving such problems, Korean Utility-Model Application Publication No. 20-2010-0006783 discloses a separable sanitary napkin comprising an absorption pad for absorbing menstrual blood and an adhesive member joined to the lower surface of the absorption pad, in which the adhesive member may be removably attached to the inner surface of the underwear. Specifically, the adhesive member may include, for example, hook-and-loop closures or double-sided tape. Here, hook-and-loop closures have to be provided to the underwear using additional adhesion means or through sewing, and thus a specific underwear (provided with hook-and-loop closures) and a specific sanitary napkin need to be used, and the above utility model is problematic because the convenience of typical sanitary napkins that may be attached or fixed to the general underwear is significantly deteriorated.

Also, Korean Utility-Model Publication No. 1995-0003985 discloses a sanitary napkin with tight strips, in which tight strips are provided at both sides of the absorption surface of the sanitary napkin contacting the human body and are formed of flexible and close-contactable resin such as silicone through coating and curing in the length direction of the sanitary napkin, and thus the tight strips made of silicone come into contact with the human body to thereby fix the movement of the sanitary napkin. This utility model pertains to a functional sanitary napkin for increasing the fixing capability of a conventional disposable sanitary napkin, and to a technique for preventing the sanitary napkin from moving by bringing the tight strips of the sanitary napkin into contact with the human body (such as the inside of a thigh).

However, the above utility model is counter to the purpose and effect of the cotton sanitary napkin, namely, that of minimizing the transfer of harmful substances to the human body and skin irritation owing to the use of cotton at the portion contacting the human body. In particular, the reason why the demand for the cotton sanitary napkin, which has to be washed in order to be used repeatedly and which is very inconvenient to stow and carry in order to be washed later, is remarkably increased among women is that the portion thereof contacting the human body is made of cotton and the waterproof sheet for the waterproofing function is configured not to contact the human body. Hence, the tight strips made of silicone, which contact the human body, are unsuitable for use in cotton sanitary napkins.

Furthermore, the above utility model is characterized in that it prevents skin rash or injury caused by friction between the sanitary napkin and the human body, but the tight strips made of silicone are constantly in contact with the human body while wearing the sanitary napkin, and thus minimal friction occurs and in particular silicone is in contact with the skin at high frictional force, so that the resultant skin rash may be more severe. No matter how soft the silicone is, if the silicone is in contact with the user's body while wearing the sanitary napkin for 3 days to 10 days, it will cause skin damage.

Moreover, users using cotton sanitary napkins adopt cotton sanitary napkins because the cotton sanitary napkins are harmless to the human body, do not irritate the skin, and feel the same as wearing cotton underwear, despite some inconveniences such as washing. Accordingly, the tight strips made of silicone, which cause a foreign feeling due to contact with the skin, are unsuitable for use in cotton sanitary napkins.

Meanwhile, urinary incontinence pads and diapers, having functions similar to sanitary napkins, have the same problems as above. Also, there is a serious problem in that urinary incontinence pads, which are mainly used for aged persons, cause more damage due to contact between various chemical substances and the skin of the aged persons, and thus the use of cotton sanitary pads is expected to increase day by day.

Therefore, it is necessary to develop a cotton sanitary pad, which is harmless to the human body and may be repeatedly used, in lieu of conventional disposable sanitary pads, and which may exhibit fixing capability and may prevent leakage of absorbate such as menstrual blood, as in the disposable sanitary pads.

CITATION LIST

Patent Literature (Patent Document 1) Korean Utility-Model Application Publication No. 20-2010-0006783
(Patent Document 2) Korean Utility-Model Publication No. 1995-0003985

SUMMARY OF THE INVENTION

Accordingly, the present invention has been made keeping in mind the problems encountered in the related art and the technical problems identified in the past.

The present inventors have recognized the above problems, have performed many experiments and studies to solve the problems, and have ascertained that, in a cotton sanitary pad configured such that a cotton lining, an absorption pad and a waterproof cover are sequentially stacked and a pair of wings is formed at both sides thereof, like a conventional cotton sanitary pad, the cotton sanitary pad is fixed to the underwear by the pair of wings, thus preventing the vertical and lateral movement of the cotton sanitary pad, and also, the outer surface of the waterproof cover, which is in contact with the underwear, is provided with a non-slip member, thus preventing the longitudinal movement of the cotton sanitary pad, thereby more effectively preventing absorbate from leaking, enabling active motion on the part of the user, and minimizing skin damage or rash on the human body, which culminates in the present invention.

Therefore, the present invention provides a non-slip cotton sanitary pad, comprising a pad body, configured such that a cotton lining, an absorption pad and a waterproof cover are sequentially stacked, and a pair of wings protruding from both sides of the pad body, in which the pair of wings protruding from both sides of the pad body includes a fastener so that the wings are fastened together in a folded state on the same surface, the cotton sanitary pad is disposed such that the waterproof cover contacts underwear, and the waterproof cover includes a non-slip member on the surface contacting the underwear.

The non-slip member is made of a silicone material, and may be thermally fused to the waterproof cover, and specifically, the silicone may be thermally fused to the surface of the waterproof cover in the form of a single continuous layer, a discontinuous pattern layer, or a mixed layer in which a continuous layer and a discontinuous pattern layer are provided in compartments.

The non-slip member may be provided on the entire surface of the waterproof cover, the pad body portion of the waterproof cover, or the wing portions of the waterproof cover.

Also, in the non-slip cotton sanitary pad according to the present invention, the fastener, which is provided to the pair of wings protruding from both sides of the pad body, may include buttons or hook-and-loop closures, and the waterproof cover may be subjected to polyurethane waterproof coating.

Particularly, the non-slip cotton sanitary pad according to the present invention may be a cotton sanitary napkin or a cotton urinary incontinence pad.

According to the present invention, a non-slip cotton sanitary pad includes a cotton lining to thus minimize skin damage due to contact with the sanitary pad, and also includes a menstrual blood (urine) absorption pad made of a natural material, thus being capable of replacing chemical sanitary pads that release harmful substances, and can be reused after being washed, which can reduce the consumption of disposable products.

Also, the cotton sanitary pad includes a pair of wings for fixing the cotton sanitary pad and a fastener provided to the wings so as to prevent vertical and lateral movement of the cotton sanitary pad, and furthermore, a non-slip member is formed on the surface of the waterproof cover that contacts the underwear, thereby effectively preventing longitudinal movement of the cotton sanitary pad even without adhesion to or contact with the human body.

The movement of the cotton sanitary pad in all possible directions is limited, whereby menstrual blood can be effectively prevented from leaking even upon small or large motions or daily activities of women wearing the same.

DESCRIPTION OF SPECIFIC EMBODIMENTS

Hereinafter, a detailed description will be given of embodiments of the present invention, which are merely set forth to illustrate the present invention but are not to be construed as limiting the scope of the present invention.

The present invention pertains to a non-slip cotton sanitary pad, comprising a pad body, configured such that a cotton lining, an absorption pad and a waterproof cover are sequentially stacked, and a pair of wings protruding from both sides of the pad body, in which the pair of wings protruding from both sides of the pad body includes a fastener so that the wings are fastened together in a folded state on the same surface, the cotton sanitary pad is disposed such that the waterproof cover contacts the underwear, and the waterproof cover includes a non-slip member on the surface contacting the underwear.

The cotton lining, the absorption pad and the waterproof cover are fixed through sewing or adhesion in the state of being sequentially stacked. In consideration of the purpose of use of the cotton sanitary pad according to the present invention, they are preferably fixed through sewing.

Specifically, the absorption pad is preferably made of a natural absorption material, especially cotton wool or cotton fiber having a predetermined thickness.

The material for the waterproof cover is not particularly limited, and may be a sheet or fabric cloth, or may be a waterproof material so that absorbate does not leak to the outside from the absorption pad after absorption of menstrual blood or urine (absorbate).

Here, it is preferred that the waterproof cover be made of a fabric cloth subjected to waterproof coating and particularly polyurethane waterproof coating.

In the non-slip cotton sanitary pad according to the present invention, the pair of wings protruding from both sides of the pad body may include a fastener so that the wings are fastened together in a folded state in the same direction.

Specifically, ends of the pair of wings are provided with the fastener, whereby the cotton sanitary pad according to the present invention is fixed to the underwear while being limited in movement in vertical and lateral directions in a manner in which the pair of wings is folded on the surface of the underwear opposite the surface contacting the cotton sanitary pad, the wings being fastened to each other by means of the fastener.

The fastener may include buttons or hook-and-loop closures. For example, snap buttons may be disposed on respective wings of the cotton sanitary pad so that the pair of wings may be fastened in a partially overlapping state. Likewise, hook-and-loop closures may be provided on respective wings of the cotton sanitary pad.

The non-slip cotton sanitary pad according to the present invention is disposed such that the waterproof cover of the cotton sanitary pad contacts the underwear, and the waterproof cover includes the non-slip member on the surface contacting the underwear. The non-slip member is formed only on the surface of the waterproof cover that is in contact with the underwear, whereby the cotton sanitary pad, which is limited in movement in vertical and lateral directions by the fastener, is also limited in movement in a longitudinal direction, ultimately ensuring stability of wearing of the cotton sanitary pad and enabling active motion of the user who wears the same.

As described above, contemporary women who repeatedly stand and sit frequently suffer from a phenomenon in which absorbate leaks to the rear, and thus the longitudinal movement of the sanitary pad is prevented, thereby effectively preventing the absorbate from leaking.

Specifically, the non-slip member is not particularly limited, so long as it is provided on the surface of the waterproof cover that is in contact with the underwear. For example, the non-slip member may be provided on the entire surface of the waterproof cover, the pad body portion of the waterproof cover, or the wing portions of the waterproof cover. Preferably, the non-slip member is provided on the pad body portion of the waterproof cover.

The non-slip member is not particularly limited, so long as it is able to prevent the longitudinal movement of the cotton sanitary pad that is placed on the underwear, and preferably, the non-slip member is made of a silicone material and may be thermally fused to the waterproof cover. Specifically, the non-slip member may be thermally fused in the form of a single continuous layer, a discontinuous pattern layer, or a mixed layer in which a continuous layer and a discontinuous pattern layer are provided in compartments.

The non-slip cotton sanitary pad according to the present invention may be a cotton sanitary napkin or a cotton urinary incontinence pad.

Below, the present invention is described in more detail with reference to the appended drawings, but the scope of the present invention is not limited thereto.

Figure 1:
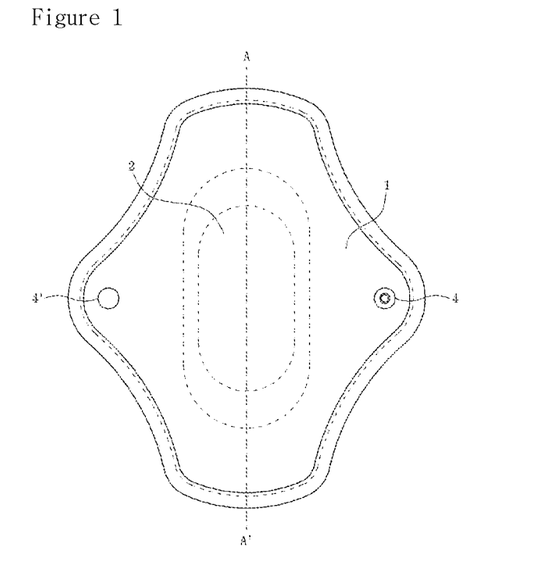
FIG. 1 is a perspective view showing the inner surface of a cotton sanitary pad according to a conventional technique and the present invention.

FIG. 1 is a perspective view showing the inner surface of a cotton sanitary pad according to a conventional technique and the present invention. With reference to FIG. 1, the cotton lining 1 is disposed on the inner surface of the cotton sanitary pad, and a pad body, which is the central portion in the length direction thereof, and a pair of wings protruding from both sides of the pad body, are shown.

The ends of the pair of wings are provided with a pair of snap buttons 4, 4', and snap buttons are provided on different surfaces of the wings so that the wings are fastened together in a folded state in the direction opposite the inner surface. For convenience, only the buttons are shown in the drawings, but hook-and-loop closures may be provided on different surfaces of the wings.

At the central portion of the pad body, the absorption pad 2 stacked under the cotton lining and the waterproof cover stacked thereunder are sewn so as to be integratedly fixed.

FIG. 1 shows the configuration of the inner surface of the cotton sanitary pad according to the present invention, which is the same as the conventional cotton sanitary pad.

Figure 2:
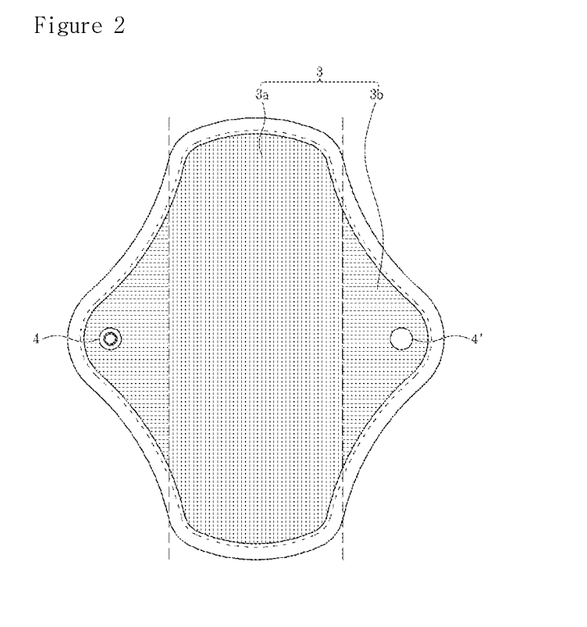
FIG. 2 is a perspective view showing the outer surface of a non-slip cotton sanitary pad according to the present invention.

FIG. 2 is a perspective view showing the outer surface of the non-slip cotton sanitary pad according to the present invention. With reference to FIGS. 1 and 2, the cotton lining 1 is positioned on the inner surface shown in FIG. 1, and the waterproof cover 3 is positioned on the outer surface shown in FIG. 2. The absorption pad 2 is interposed between the cotton lining and the waterproof cover. As shown in FIG. 2, the waterproof cover 3 constituting the outer surface of the cotton sanitary pad is formed so as to be the same size as the cotton lining 1, and functions to prevent not only the absorbate in the absorption pad 2 but also the absorbate in the inner surface of the cotton sanitary pad from flowing to the underwear or leaking to the outside.

The waterproof cover 3 shown in FIG. 2 comes into contact with the underwear, and in order to prevent the cotton sanitary pad from moving from the underwear, the entire surface 3a+3b of the waterproof cover may be provided with the non-slip member. Alternatively, even when the non-slip member is provided on the pad body portion 3a of the waterproof cover or the wing portions 3b of the waterproof cover, it is possible to prevent the longitudinal movement of the non-slip cotton sanitary pad.

Figure 3:
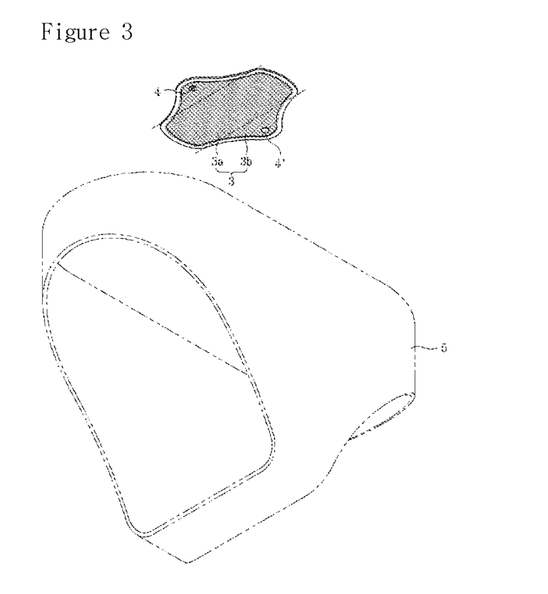
FIGS. 3 and 4 show the non-slip cotton sanitary pad according to the present invention before and after application to the underwear.
Figure 4:
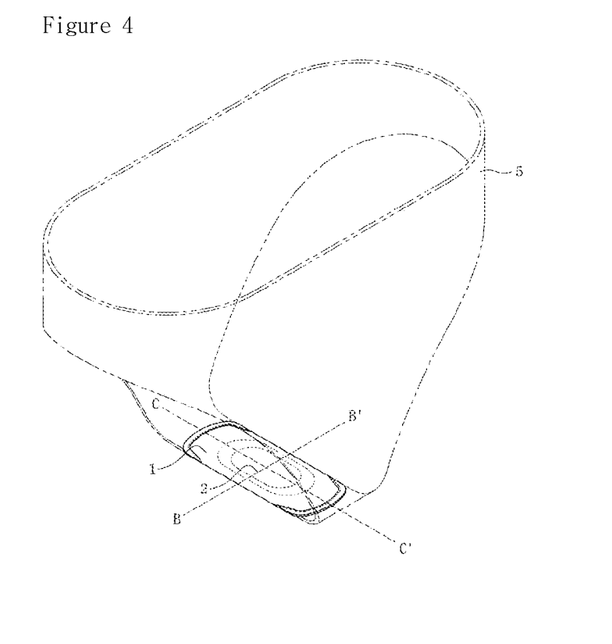

FIGS. 3 and 4 illustrate the non-slip cotton sanitary pad according to the present invention, which is applied to the underwear.

With reference to FIGS. 3 and 4, the outer surface of the non-slip cotton sanitary pad according to the present invention, that is, the surface on which the waterproof cover 3 is positioned, is disposed so as to contact the underwear 5. The pair of wings is fastened on the surface of the underwear opposite the surface contacting the cotton sanitary pad, whereby the cotton sanitary pad is primarily fixed, and thus the movement thereof is prevented in vertical and lateral directions. The longitudinal movement of the non-slip cotton sanitary pad is effectively prevented by the non-slip member provided on the outer surface of the waterproof cover. Although prevention only of the longitudinal movement by the non-slip member is described, the lateral movement may also be more effectively prevented.

Figure 5:
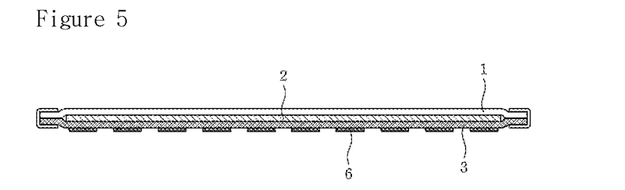
FIG. 5 is a cross-sectional view in a longitudinal direction of the non-slip cotton sanitary pad according to the present invention, taken along line A-A' of FIG. 1.

FIG. 5 is a cross-sectional view in a longitudinal direction of the non-slip cotton sanitary pad according to the present invention, taken along the line A-A' of FIG. 1.

With reference to FIGS. 1 and 5, the cotton lining, the absorption pad, and the waterproof cover are sequentially stacked downwards and sewn, and the outer circumferential surface of the cotton sanitary pad is further sewn with a finishing material. The absorption pad may be configured to be positioned at the central portion with which the absorbate first comes into contact, and if necessary, the cotton lining and the waterproof cover may be formed so as to be the same size.

The non-slip member is positioned on the surface of the waterproof cover opposite the surface contacting the absorption pad, and a discontinuous layer may be illustrated in the drawing, but a single continuous layer may alternatively be provided.

Figure 6:
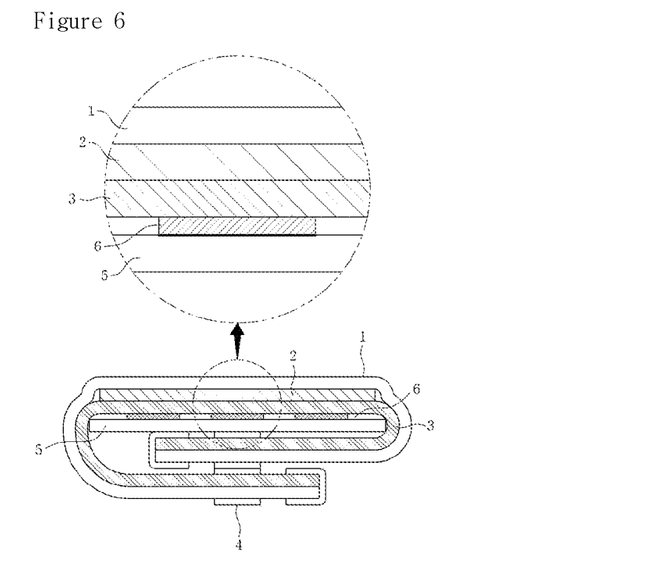
FIG. 6 is a cross-sectional view in a lateral direction of the non-slip cotton sanitary pad, taken along line B-B' of FIG. 4.

FIG. 6 is a cross-sectional view in a lateral direction of the non-slip cotton sanitary pad, taken along the line B-B' of FIG. 4.

With reference to FIGS. 4 and 6, the cotton sanitary pad is placed on the surface of the underwear that contacts the human body so that the waterproof cover 3 and the non-slip member 6 are in contact therewith, and the pair of wings of the cotton sanitary pad is fixed by the fastener 4 in a folded state on the opposite surface thereof.

Accordingly, the cotton sanitary pad is prevented from being separated from the underwear 5, and vertical movement thereof is prevented. Briefly, the cotton sanitary pad is allowed to come into close contact with the surface of the underwear between the human body and the underwear.

Figure 7A:
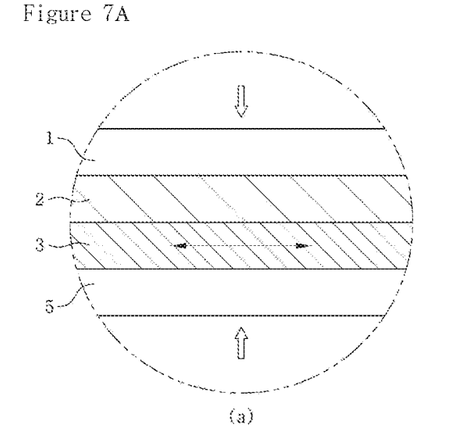
FIGS. 7A and 7B schematically show the lateral movement of the conventional cotton sanitary pad and the non-slip cotton sanitary pad according to the present invention when applied to underwear.
Figure 7B:
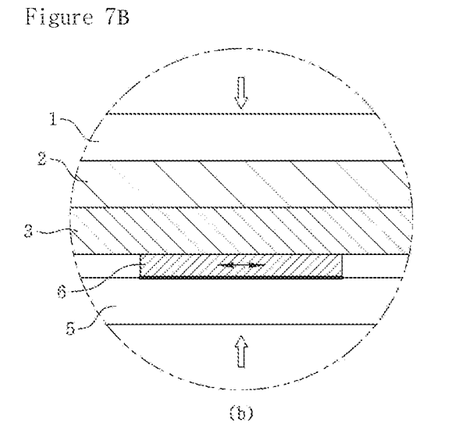

FIGS. 7A and 7B schematically show the lateral movement of the conventional cotton sanitary pad and the non-slip cotton sanitary pad according to the present invention when applied to the underwear.

As described above, the cotton sanitary pad according to the present invention may be fixed to the underwear by means of the pair of wings and the fastener provided therein, and furthermore, the lateral movement of the pad body may be prevented. The pair of wings and the fastener are also provided in a conventional cotton sanitary pad, whereby the lateral movement and the vertical movement of the cotton sanitary pad may be prevented. However, the cotton sanitary pad according to the present invention may further include the non-slip member on the outer surface of the waterproof cover, that is, on the surface of the cotton sanitary pad contacting the underwear, thus more effectively preventing lateral movement thereof.

In particular, although the sanitary pad may be manufactured so as to have a size or shape that varies depending on the amount of the absorbate and the physical body of a user, it is preferred that the size and shape of a typical cotton sanitary pad be maintained in terms of carrying ability, absorption efficiency of the absorbate and ease of manufacture. Thus, the cotton sanitary pad according to the present invention has the same size and shape as a conventional cotton sanitary pad and is characterized by reduced leakage of the absorbate by preventing the movement of the cotton sanitary pad.

FIGS. 7A and 7B schematically show the lateral movement of the conventional cotton sanitary pad and the cotton sanitary pad according to the present invention, in which the lateral movement of each of the cotton sanitary pads is represented by the arrow.

The pressure of the upper and lower surfaces of the cotton sanitary pad and the frictional force between the underwear and the waterproof cover from the pair of wings and the fastener of the cotton sanitary pad are the same as or similar to the conventional cotton sanitary pad, but the cotton sanitary pad according to the present invention further includes the non-slip member on the surface of the waterproof cover, thereby creating frictional force between the non-slip member and the underwear, ultimately significantly reducing the lateral movement of the cotton sanitary pad.

The material for the non-slip member is not particularly limited, so long as it has higher frictional force with the underwear than with the waterproof cover, and examples thereof may include rubber, silicone, or a polymer material. Considering that the cotton sanitary pad is intended to eliminate chemical substances as much as possible to reduce harm to the human body, a silicone material is preferably used.

The non-slip member is disposed between the waterproof cover and the underwear, and the material thereof is not limited, so long as it is able to reduce the movement of the cotton sanitary pad due to the frictional force between the underwear and the non-slip member. Taking into consideration the purpose of use of the cotton sanitary pad, namely, eliminating the use of adhesive or double-sided tape comprising chemical components, unlike disposable sanitary pads, the non-slip member is preferably added in a manner in which the silicone member is thermally fused to the surface of the waterproof cover without the use of adhesion means. The waterproof cover is made of a material subjected to waterproof coating in order to prevent the re-release of the absorbate, and the silicone member may be thermally fused to the surface of the waterproof cover.

The material for the waterproof cover, which is subjected to waterproof coating, is not particularly limited, so long as it is able to prevent menstrual blood or urine containing water from being re-released from the absorption pad. Preferably, it is subjected to polyurethane waterproof coating.

Figure 8:
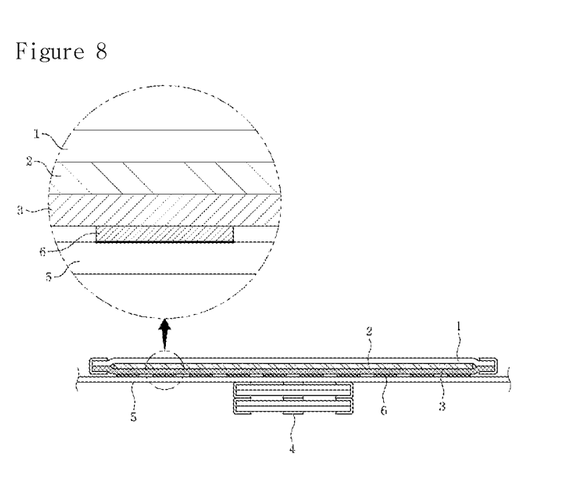
FIG. 8 is a cross-sectional view in a longitudinal direction of the non-slip cotton sanitary pad, taken along line C-C' of FIG. 4.

FIG. 8 is a cross-sectional view in a longitudinal direction of the non-slip cotton sanitary pad, taken along the line C-C' of FIG. 4.

By the pair of wings and the fastener of the cotton sanitary pad, only the central portion of the pad body of the cotton sanitary pad may be fixed to the underwear, and thus the longitudinal movement of the cotton sanitary pad may become problematic.

Figure 9A:
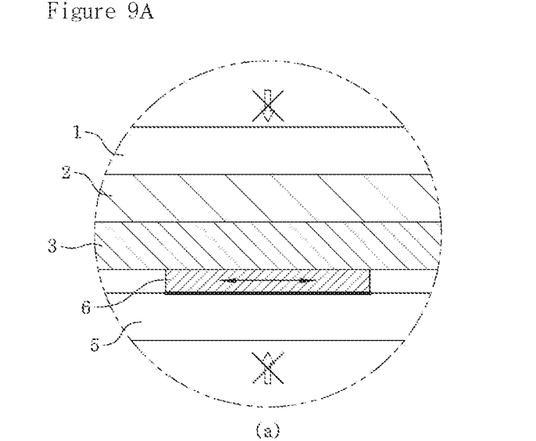
FIGS. 9A and 9B schematically show the longitudinal movement of the conventional cotton sanitary pad and the non-slip cotton sanitary pad according to the present invention when applied to underwear.
Figure 9B:
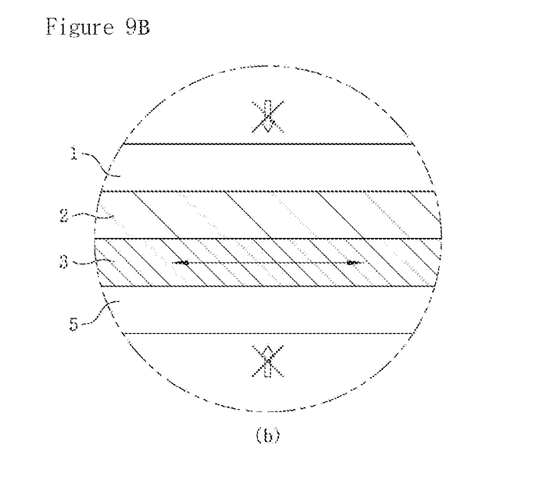

The longitudinal movement of the conventional cotton sanitary pad and the cotton sanitary pad according to the present invention is shown in FIGS. 9A and 9B. FIGS. 9A and 9B schematically show the longitudinal movement of the conventional cotton sanitary pad and the non-slip cotton sanitary pad according to the present invention when applied to underwear, in which the pair of wings and the fastener, which are used to fix only the central portion of the pad body of the cotton sanitary pad, function to indirectly fix the front portion and the back portion of the pad body to the underwear, and thus almost no pressure is applied to the upper and lower surfaces of the cotton sanitary napkin by the pair of wings and the fastener.

Accordingly, the longitudinal movement of the cotton sanitary pad depending on the motion of the user becomes greater. The cotton sanitary pad moves longitudinally even upon sitting or standing motions or light walking motions, which are considered states of low activity, and the problems in which absorbate flows not to the cotton sanitary pad but to the underwear easily occur.

However, the cotton sanitary pad according to the present invention includes the non-slip member, whereby frictional force is created between the non-slip member and the underwear, thus significantly reducing the longitudinal movement of the cotton sanitary pad.

Figure 10:
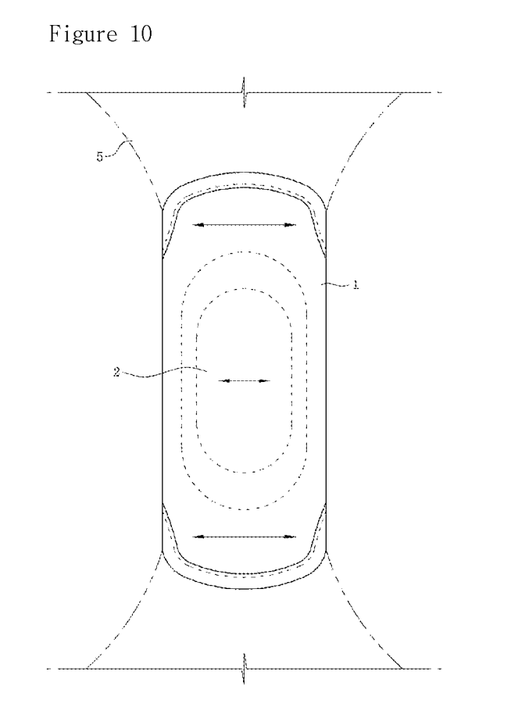
FIG. 10 schematically shows the lateral movement of the conventional cotton sanitary pad when applied to underwear.

FIG. 10 schematically shows the lateral movement of the conventional cotton sanitary pad when applied to underwear.

As described above, the pair of wings and the fastener, which are provided to the conventional cotton sanitary pad, function to fix the cotton sanitary pad to the underwear, thus preventing both vertical movement and lateral movement of the cotton sanitary pad.

As shown in FIG. 10, however, the pair of wings and the fastener of the cotton sanitary pad are used to directly fix only the central portion of the cotton sanitary pad to the underwear and to indirectly fix the front portion and the back portion of the cotton sanitary pad, and the lateral movement of the cotton sanitary pad is much greater at the front portion and the back portion of the cotton sanitary pad than at the central portion thereof.

Leakage of the absorbate from the sanitary pad occurs frequently at the user's hips, which are pointed out, and is thus the main reason why users are reluctant to use cotton sanitary pads.

In the shape of typical underwear, it is difficult to directly provide the fixing means to the front portion and the back portion of the cotton sanitary pad. Unlike the disposable sanitary pad, having the direct fixing means using an adhesive or double-sided tape, the cotton sanitary pad makes it impossible to use an adhesive or double-sided tape, which is a temporary and short-term fixing means and is harmful to the human body, making it difficult to limit the movement of the front portion and the back portion of the cotton sanitary pad.

In the cotton sanitary pad according to the present invention, the non-slip member is provided on the outer surface of the waterproof cover, thereby further increasing the frictional force between the cotton sanitary pad and the underwear to thus further limit the movement of the front portion and the back portion of the cotton sanitary pad, thereby significantly reducing the leakage of absorbate. Moreover, the foreign sensation upon use of the cotton sanitary pad is decreased and the fit of the cotton sanitary pad is further increased because the cotton sanitary pad and the underwear may be integratedly joined.

Figure 11:
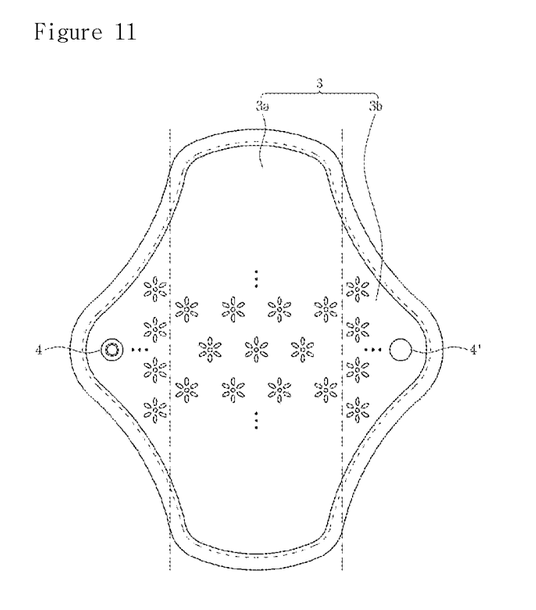
FIG. 11 schematically shows a non-slip cotton sanitary pad according to an exemplary embodiment of the present invention.

FIG. 11 schematically shows a non-slip cotton sanitary pad according to an exemplary embodiment of the present invention.

In the cotton sanitary pad according to the present invention, the non-slip member is not particularly limited in the shape or area thereof, so long as it is provided to the surface of the waterproof cover, and the frictional force with the underwear may be increased by the addition of the non-slip member.

For example, the non-slip member may be thermally fused to the entire surface of the waterproof cover, the non-slip member being in the form of a single continuous layer, a discontinuous pattern layer, or a mixed layer in which a continuous layer and a discontinuous pattern layer are provided in compartments.

FIG. 11 illustrates the non-slip cotton sanitary pad according to an exemplary embodiment of the present invention, in which the discontinuous pattern layer is formed on the entire surface of the waterproof cover. Although the non-slip member is formed in a discontinuous pattern at a predetermined interval on the entire surface of the waterproof cover in FIG. 11, it is possible to form the non-slip member only on the specific portion of the cotton sanitary pad. More specifically, the non-slip member may be formed only on the pad body portion of the waterproof cover, the wing portions of the waterproof cover, part of the pad body portion of the waterproof cover, or part of the wing portions of the waterproof cover.

A better understanding of the present invention will be given through the following examples, which are not to be construed as limiting the scope of the present invention.

Manufacture of Cotton Sanitary Napkin

Comparative Example

A sanitary napkin, configured to include a porous cotton (a cotton lining), a cotton absorbent sheet (an absorption pad), and a polyurethane coating cotton (a waterproof cover), was manufactured.

Example

A cotton sanitary napkin was manufactured in the same configuration and manner as in Comparative Example, with the exception that a non-slip member made of a silicone material was thermally fused to the entire surface of the polyurethane coating cotton subjected to polyurethane coating treatment.

Panel Test

Among 200 women in their 20s to 50s having similar menstrual cycles for one year (an average menstrual period of 4 to 5 days, and upon continuous menstruation without menstrual irregularity, the period between the first day of menstruation and the first day of the next menstrual period was 27 to 29 days on average), 124 women who i) had never used a cotton sanitary napkin, ii) suffered from menstrual irregularities at least five times during the past year and from menstrual pain every menstrual period, and iii) had used 4 to 6 disposable sanitary napkins (mid-size) during menstruation were subjected to the following tests.

The first questionnaire was conducted after using the cotton sanitary napkin of Comparative Example for 3 months, and then the second questionnaire was carried out after using the cotton sanitary napkin of Example for 3 months. The results of each questionnaire were as follows. Each test was carried out by instructing all subjects to comply with the condition of replacing the mid-size sanitary napkin every 3 hours (with an error range of about 30 min), except when sleeping.

<First Questionnaire>

1) Compared with the use of a conventional disposable sanitary napkin, differences in menstrual irregularity, menstrual pain, skin symptoms and fit after using the cotton sanitary napkin of Comparative Example were evaluated, scored in the range from 1 to 5, and averaged.

TABLE 1

|  | Menstrual irregularity improvement | Menstrual pain improvement | Skin symptom improvement | Fit | Comfort |
|---|---|---|---|---|---|
| Average score | 2.25 | 4.45 | 3.75 | 4.68 | 2.61 |
| Multiple comments | The menstrual cycle and the menstruation period seemed to be uniform (34 women) | In the first month, menstrual pain was significantly reduced, and there was almost no pain after 3 months of use (55 women) | Skin itching was eliminated (39 women) | Similar to wearing underwear (88 women) | Anxiety due to movement of back portion of cotton sanitary napkin (108 women) |

(1: no difference~5: great difference)

Regarding the improvement in menstrual irregularity, the period of use of the cotton sanitary napkin of Comparative Example was somewhat short, namely 3 months, and thus the users did not feel much difference in improvement, but there were multiple comments stating that the menstrual cycle (the period between the first day of the menstrual period and the first day of the next menstrual period) and the menstrual period became uniform similarly to those in the past without menstrual irregularities.

Most users felt that the improvement in menstrual pain was obvious in the first month, and the improvement in menstrual pain was felt by most users, with only a difference in the extent of improvement. In particular, there were no subjects who did not feel any improvement after using the cotton sanitary napkin of Comparative Example for 3 months compared to when using disposable sanitary napkins.

Regarding the improvement in skin symptoms, all of the 124 women responded that they had experienced slight itching and severe skin rash in the preliminary survey conducted before the present test, but also responded that, in the first questionnaire, there was improvement in skin symptoms, including multiple comments that itching symptoms were immediately improved.

Regarding the improvement in fit, there were multiple comments stating that the cotton sanitary pad, comprising the cotton lining, exhibited a tactile sensation similar to that of underwear. Despite having a similar fit to the underwear, there was inconvenience due to the movement of the cotton sanitary napkin during activity, and comfort at the time of wearing was somewhat deteriorated.

In addition, the opinions of most users were that an odor reduction effect during menstruation was exhibited compared to when using the conventional disposable sanitary napkin.

Therefore, compared with the conventional disposable sanitary napkin, the cotton sanitary napkin of Comparative Example was remarkably improved in menstrual pain, skin symptoms and fit and helped reduce odors, but was impossible to wear comfortably because of the problem in which the cotton sanitary napkin moved upon motion of the user, whereby menstrual blood leaked.

2) The frequency of leakage of menstrual blood and the portion at which menstrual blood leaked during the menstrual period when using the cotton sanitary napkin of Comparative Example compared to when using the conventional disposable sanitary napkin were evaluated. The results are as follows.

TABLE 2

|  | Average number of occurrences of menstrual blood leakage during one menstrual period (/day) | | Portion at which menstrual blood mainly leaks | Activity during which menstrual blood leakage occurs (multiple responses allowed) |
| --- | --- | --- | --- | --- |
|  | Conventional disposable sanitary napkin | Cotton sanitary napkin of Comparative Example | | |
|  | 0.4 times | 2 times | Back portion of cotton sanitary napkin | When sitting (55 women) When walking (35 women) When sleeping (100 women) |
| Multiple comments | About 2 instances of leakage on average during the entire menstrual period | Menstrual blood leakage when sleeping (120 women) | | |

As is apparent from the above results, compared to the conventional disposable sanitary napkin, the cotton sanitary napkin of Comparative Example frequently caused the leakage of menstrual blood, which was confirmed to be a factor in inhibiting the comfortable wearing of the cotton sanitary napkin as described in 1) above.

In particular, regardless of the posture at bedtime, the phenomenon of menstrual blood leakage upon sleeping occurred in most subjects, and specifically, menstrual blood leakage was observed in the back portion of the cotton sanitary napkin, which was considered to be because the front and back portions of the cotton sanitary napkin, using the pair of wings and the fastener, without any direct fixing means, moved very large distances in longitudinal and lateral directions, and thus the position of the cotton sanitary napkin departed from the portion at which menstrual blood flows.

Furthermore, the menstrual blood easily leaked even in daily life, such as when walking or sitting, in addition to when sleeping.

<Second Questionnaire>

1) Compared with the use of a conventional disposable sanitary napkin, differences in menstrual irregularity, menstrual pain, skin symptoms and fit after a total of 6 months using the cotton sanitary napkin of Comparative Example for 3 months and the cotton sanitary napkin of Example for 3 months were evaluated, scored in the range from 1 to 5, and averaged.

TABLE 3

|  | Menstrual irregularity improvement | Menstrual pain improvement | Skin symptom improvement | Fit | Comfort |
| --- | --- | --- | --- | --- | --- |
| Average score | 4.00 | 4.68 | 4.25 | 4.83 | 4.83 |
| Multiple comments | The menstrual cycle and the | In the first month, menstrual | Skin itching was eliminated | Similar to wearing | Movement of back |

TABLE 3-continued

| Menstrual irregularity improvement | Menstrual pain improvement | Skin symptom improvement | Fit | Comfort |
|---|---|---|---|---|
| menstruation period seemed to be uniform (81 women) | pain was significantly reduced, and there was almost no pain after 6 months of use (93 women) | (89 women) | underwear (92 women) | portion of cotton sanitary napkin was significantly reduced (112 women) |

(1: no difference~5: great difference)

2) The frequency of leakage of menstrual blood and the portion at which menstrual blood leaked during the menstrual period when using the cotton sanitary napkin of Example compared to when using the cotton sanitary napkin of Comparative Example were evaluated. The results are as follows.

TABLE 4

| | Average number of occurrences of menstrual blood leakage during one menstrual period (/day) | | Portion at which menstrual blood mainly leaks | Activity during which menstrual blood leakage occurs (multiple responses allowed) |
|---|---|---|---|---|
| | Cotton sanitary napkin of Comparative Example | Cotton sanitary napkin of Example | | |
| | 2 times | 0.5 times | Back portion of cotton sanitary napkin (68 women) | When sleeping (62 women) (When sitting (24 women) |
| Multiple comments | Menstrual blood leakage when sleeping (120 women) | About 2~3 instances of leakage on average during the entire menstrual period | | |

In the second questionnaire, the number of subjects who felt that menstrual irregularity, menstrual pain, skin symptoms, fit and comfort were all improved compared to those using conventional disposable sanitary napkins increased, and the average scores also increased overall.

In particular, improvements in menstrual irregularity, menstrual pain, and skin symptoms were regarded as major advantages of using cotton sanitary napkins, obtained by using the cotton sanitary napkin for a long period of time, and fit and comfort were remarkably improved compared to when using the cotton sanitary napkin of Comparative Example. It was concluded that the cotton sanitary napkin of Example was evaluated at a higher score when the cotton sanitary napkin of Example was used immediately after the cotton sanitary napkin of Comparative Example, which had no silicone non-slip member and was thus uncomfortable.

In spite of the relative effect of this order of use, the case where the cotton sanitary napkin of Example was separated from the underwear and moved independently was very rare in most subjects, and thus a high score of improvement was obtained along with the opinion that the fit was very good, and the effect of inhibiting the movement of the cotton sanitary napkin by the addition of the non-slip member remarkably increased the fit and comfort during wearing.

In the above 2) of the second questionnaire, the number of occurrences of daily average menstrual blood leakage was significantly reduced to nearly a quarter, and thus it was confirmed that the leakage of menstrual blood almost never occurred to the same level as that when using a conventional disposable sanitary napkin.

Furthermore, when using the cotton sanitary napkin of Comparative Example, the leakage of menstrual blood mainly occurred in the back portion of the cotton sanitary napkin, that is, the hip portion, and compared to the results of the first questionnaire, which showed that menstrual blood leakage was observed in all activities, such as when sleeping, sitting, walking, etc., no leakage was observed during walking, and the number of subjects who were observed to have leakage when sitting and when sleeping was greatly reduced.

Therefore, the cotton sanitary napkin of Example includes the non-slip member on the outer surface of the waterproof cover contacting the underwear, whereby the longitudinal movement of the cotton sanitary napkin is prevented, and the lateral movement of the front and back portions of the cotton sanitary napkin is also prevented, thus effectively preventing the leakage of menstrual blood and improving fit and comfort when wearing.

Although embodiments of the present invention have been described with reference to the accompanying drawings, those skilled in the art will appreciate that the present invention may be embodied in other specific forms without changing the technical spirit or essential features thereof. Thus, the embodiments described above should be understood to be non-limiting and illustrative in every way.

What is claimed is:

1. A non-slip reusable cotton-lined sanitary pad, comprising:
   a pad body, configured such that a cotton lining, an absorption pad and a waterproof cover are sequentially stacked, and
   a pair of wings protruding from both sides of the pad body,
   wherein the pair of wings protruding from both sides of the pad body includes a fastener so that the wings are fastened together in a folded state on the same surface,
   wherein a non-slip member is provided on an outer surface of the waterproof cover such that the non-slip member is disposed between the waterproof cover and an underwear,
   the non-slip member is made of a silicone material, and is thermally fused to the waterproof cover,
   the fastener includes buttons or hook-and-loop closures, and
   the waterproof cover is subjected to polyurethane waterproof coating.

2. The non-slip reusable cotton-lined sanitary pad of claim 1, wherein the non-slip member is formed on an entire surface of the waterproof cover, a pad body portion of the waterproof cover, or wing portions of the waterproof cover.

3. The non-slip reusable cotton-lined sanitary pad of claim 1, wherein the non-slip member is thermally fused to the surface of the waterproof cover, the non-slip member being in a form of a single continuous layer, a discontinuous pattern layer, or a mixed layer in which a continuous layer and a discontinuous pattern layer are provided in compartments.

4. The non-slip reusable cotton-lined sanitary pad of claim 1, wherein the cotton sanitary pad is a cotton sanitary napkin or a cotton urinary incontinence pad.

5. The non-slip reusable cotton-lined sanitary pad of claim 1, wherein the cotton lining is positioned on an inner surface of the cotton sanitary pad.

6. The non-slip reusable cotton-lined sanitary pad of claim 1, wherein the absorption pad is made out of a natural absorption material.

7. The non-slip reusable cotton-lined sanitary pad of claim 6, wherein the natural material is cotton wool or cotton fiber.

8. The non-slip reusable cotton-lined sanitary pad of claim 1, wherein the waterproof cover is made out of a sheet or fabric cloth subjected to the polyurethane waterproof coating.

9. The non-slip reusable cotton-lined sanitary pad of claim 1, wherein the waterproof cover constituting the outer surface of the sanitary pad is formed so as to be the same size as the cotton lining.

10. The non-slip reusable cotton-lined sanitary pad of claim 1, wherein the non-slip member composed of the silicone non-slip material has a higher frictional force with the underwear than with the waterproof cover.

11. The non-slip reusable cotton-lined sanitary pad of claim 1, wherein the silicone non-slip member may further include rubber or polymer materials.

12. The non-slip reusable cotton-lined sanitary pad of claim 1, wherein a central portion of the pad body including the absorption pad stacked under the cotton lining and the waterproof cover stacked thereunder are integratedly fixed through sewing or adhesion by the state of being sequentially stacked.

13. The non-slip reusable cotton-lined sanitary pad of claim 1, wherein the absorption pad, cotton lining, and waterproof cover are integratedly fixed through sewing.

14. The non-slip reusable cotton-lined sanitary pad of claim 1, wherein an outer circumferential surface of the sanitary pad is further sewn with a finishing material.

15. The non-slip reusable cotton-lined sanitary pad of claim 1, wherein the cotton sanitary pad is free of adhesives or adhesive members comprising chemical components not limited to those commonly in double-sided tape.

16. The non-slip reusable cotton-lined sanitary pad of claim 1, wherein the cotton sanitary pad is manufactured in a variety of sizes and shapes to suit the physical body size of the user and/or to suit the amount of absorbate by the user.

17. The non-slip reusable cotton-lined sanitary pad of claim 1, wherein the cotton sanitary pad may be repeatedly reused after washing.

18. The non-slip reusable cotton-lined sanitary pad of claim 1, wherein the buttons or hook-and-loop closures are positioned on a location on the wings to prevent vertical and lateral movement of the cotton sanitary pad.

19. The non-slip reusable cotton-lined sanitary pad of claim 18, wherein the non-slip member further prevents the longitudinal movement of the cotton sanitary pad by creating a frictional force between the non-slip member and the underwear.

20. The non-slip reusable cotton-lined sanitary pad of claim 19, wherein leakage of absorbate is reduced due to the combination of the buttons or the hook-and-loop closures, the wings, and the non-slip member, as compared to conventional, disposable sanitary pads.

* * * * *